(12) United States Patent
Dirienzi et al.

(10) Patent No.: US 10,341,489 B1
(45) Date of Patent: Jul. 2, 2019

(54) AGENT APPLICATION AND INTEGRATED CALL PROCESSING PLATFORM

(71) Applicant: West Corporation, Omaha, NE (US)

(72) Inventors: Jonathan R. Dirienzi, Eagleville, PA (US); Jonathan Levine, Chesterbrook, PA (US); Eric Weaver, West Chester, PA (US)

(73) Assignee: West Corporation, Omaha, NE (US)

( * ) Notice: Subject to any disclaimer, the term of this patent is extended or adjusted under 35 U.S.C. 154(b) by 21 days.

(21) Appl. No.: 15/605,607

(22) Filed: May 25, 2017

(51) Int. Cl.
| H04M 3/51 | (2006.01) |
| H04M 3/523 | (2006.01) |
| G06Q 30/00 | (2012.01) |
| G06F 19/00 | (2018.01) |
| G16H 10/60 | (2018.01) |

(52) U.S. Cl.
CPC ......... H04M 3/5183 (2013.01); H04M 3/523 (2013.01); G06F 19/328 (2013.01); G06Q 30/016 (2013.01); G16H 10/60 (2018.01)

(58) Field of Classification Search
CPC ........... H04M 3/42059; H04M 3/5183; H04M 3/5166; H04M 3/523; H04M 3/436; H04M 3/4936
See application file for complete search history.

(56) References Cited

U.S. PATENT DOCUMENTS

| 7,050,567 | B1* | 5/2006 | Jensen | H04M 3/5232 379/265.13 |
| 8,976,939 | B1* | 3/2015 | Hamilton | H04M 3/5116 379/45 |
| 9,392,115 | B2* | 7/2016 | Ristock | H04M 3/5232 |
| 2006/0153356 | A1* | 7/2006 | Sisselman | H04M 3/5233 379/265.12 |
| 2009/0190749 | A1* | 7/2009 | Xie | H04M 3/5232 379/266.01 |
| 2014/0094134 | A1* | 4/2014 | Balthasar | H04M 3/5235 455/404.1 |

* cited by examiner

*Primary Examiner* — Nafiz E Hoque

(57) ABSTRACT

Agents operating at call centers or other customer support service networks may assist large numbers of customers consecutively and in a dynamic manner. One example may include receiving a number of calls for customer service support from a corresponding number of customer devices at a call server, prioritizing an order of the calls based on the parsed content, assigning the calls to corresponding agent devices, and modifying the order of the calls based on changes to at least one of the customer status and agent availability.

20 Claims, 17 Drawing Sheets

820

840

850

AGENT APPLICATION AND INTEGRATED CALL PROCESSING PLATFORM

CROSS-REFERENCE TO RELATED APPLICATION

This application is related to co-pending application Nos. PAT-273A and PAT-273B, the entire contents of which are hereby incorporated by reference.

TECHNICAL FIELD OF THE APPLICATION

This application relates to an agent application for receiving and handling call processing events and more particularly to an agent user interface for automated and dynamic call processing functions for optimal customer call routing.

BACKGROUND OF THE APPLICATION

Conventionally, when a customer calls a call center or agent support system for reasons related to a paid service or other business entity, the call agent or agent phone support system has a combination of a phone and computer database interface to identify the caller and reference any account information necessary to confirm subscriptions, update user accounts, add/remove services, etc.

As the types of customer subscriptions continues to evolve, the types of call agent services and call center services continues to evolve as well. For instance, the less time taken to route a caller to the correct agent having the correct skills will optimize caller satisfaction. Also, the customers prefer to have quick and simple access to any type of account service including upgrades, downgrades, technical support, etc.

FIG. 1 illustrates a conventional prior art network configuration 100. Referring to FIG. 1, the consumer 102 may utilize any type of communication device 110, such as a phone, mobile phone, smartphone, Internet enabled computing device, tablet computing device, etc., to initiate a communication to a customer call center over a network or PSTN 130. The service provider 120 may be located at a remote service site managed by call database servers 124. The service agent 122 typically sits at work and answers a line phone 123 as the calls and requests are received. This approach does not enable a customized computing approach or a portable computing approach to responding to customer service calls.

SUMMARY OF THE APPLICATION

Example embodiments of the present application provide a method that includes populating a portion of a first agent user interface of a first agent device with a first customer profile, identifying a second agent device currently assigned a second customer call with second customer call information related to the first customer call information, comparing the first customer call information to the second customer call information, determining the second customer call information exceeds a relevancy threshold when compared to first customer call information, populating a portion of a second agent user interface of the second agent device with the portion of the first agent user interface, and updating the first agent user interface by removing the first customer call information and providing another customer call to the first user agent device.

Another example embodiment may include an apparatus that provides a processor configured to populate a portion of a first agent user interface of a first agent device with a first customer profile, identify a second agent device currently assigned a second customer call with second customer call information related to the first customer call information, compare the first customer call information to the second customer call information, determine the second customer call information exceeds a relevancy threshold when compared to first customer call information, populate a portion of a second agent user interface of the second agent device with the portion of the first agent user interface, and update the first agent user interface by removing the first customer call information and providing another customer call to the first user agent device.

Yet another example embodiment may include a non-transitory computer readable storage medium configured to store instructions that when executed causes a processor to perform populating a portion of a first agent user interface of a first agent device with a first customer profile, identifying a second agent device currently assigned a second customer call with second customer call information related to the first customer call information, comparing the first customer call information to the second customer call information, determining the second customer call information exceeds a relevancy threshold when compared to first customer call information, populating a portion of a second agent user interface of the second agent device with the portion of the first agent user interface, and updating the first agent user interface by removing the first customer call information and providing another customer call to the first user agent device.

Still another example embodiment may include a method that includes receiving a plurality of calls for customer service support from a corresponding plurality of customer devices at a call routing server, retrieving user profiles associated with the plurality of calls and identifying call information for the plurality of calls, determining at least one call is associated with a first user profile having a task deadline approaching sooner than the other user profiles, and establishing a priority for the at least one call to be processed by an agent device.

Still yet a further example embodiment may include an apparatus that includes a receiver configured to receive a plurality of calls for customer service support from a corresponding plurality of customer devices at a call routing server, a processor configured to retrieve user profiles associated with the plurality of calls and identifying call information for the plurality of calls, determine at least one call is associated with a first user profile having a task deadline approaching sooner than the other user profiles, and establish a priority for the at least one call to be processed by an agent device.

Still yet another example embodiment may include a non-transitory computer readable storage medium configured to store instructions that when executed causes a processor to perform receiving a plurality of calls for customer service support from a corresponding plurality of customer devices at a call routing server, retrieving user profiles associated with the plurality of calls and identifying call information for the plurality of calls, determining at least one call is associated with a first user profile having a task deadline approaching sooner than the other user profiles, and establishing a priority for the at least one call to be processed by an agent device.

Still yet a further example embodiment may include a method that includes receiving a plurality of calls for customer service support from a corresponding plurality of customer devices at a call server, prioritizing an order of the plurality of calls based on the parsed content, assigning the plurality of calls to a corresponding plurality of agent devices, and modifying the order of the plurality of calls based on changes to at least one of the customer status and agent availability.

Still yet a further example embodiment may include an apparatus that provides receiving a plurality of calls for customer service support from a corresponding plurality of customer devices at a call server, prioritizing an order of the plurality of calls based on the parsed content, assigning the plurality of calls to a corresponding plurality of agent devices, and modifying the order of the plurality of calls based on changes to at least one of the customer status and agent availability.

Still yet another example embodiment may include a non-transitory computer readable storage medium configured to store instructions that when executed causes a processor to perform receiving a plurality of calls for customer service support from a corresponding plurality of customer devices at a call server, prioritizing an order of the plurality of calls based on the parsed content, assigning the plurality of calls to a corresponding plurality of agent devices, and modifying the order of the plurality of calls based on changes to at least one of the customer status and agent availability.

DETAILED DESCRIPTION OF THE APPLICATION

Figure 1:
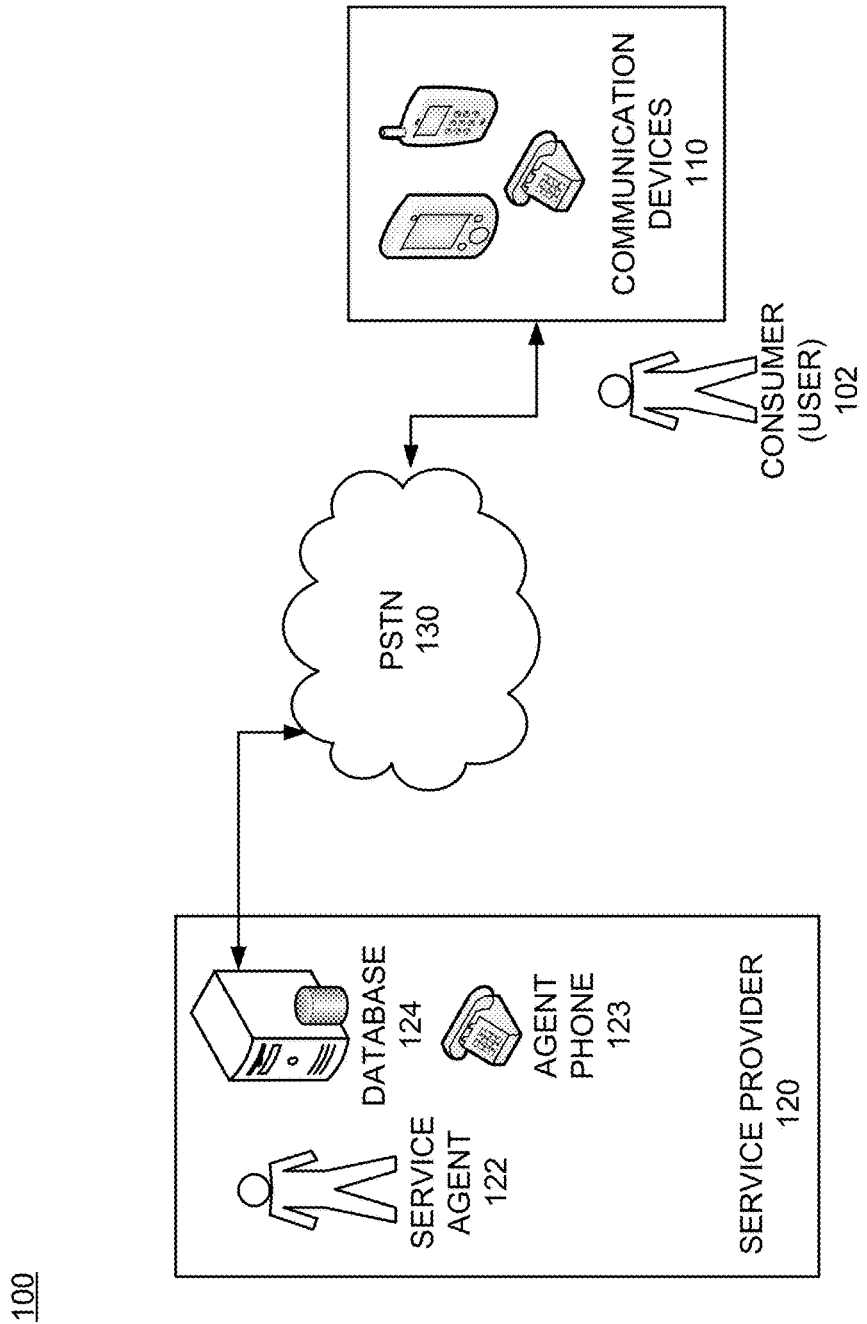
FIG. 1 illustrates an example prior art communication network for customer request processing.

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

Example embodiments include an agent desktop application that integrates the agent desktop and a customer communication system. The application permits agents to efficiently service incoming member phone calls efficiently using a combination of their phone device, and/or a 'softphone' application and toolbar. Certain features of the agent desktop application may include a display interface that is non-browser enabled or browser enabled, two-way communication with customer records databases that permits tabs to be accessed, shared and transferred, and integration into existing contact center applications enabling various key efficiencies. For instance, drop-down menu options of active agents for easy direct transfers, active skillsets for easy transfers, transfer and conference to an agent, skillset or external number identification, on-hold timer with escalation indicator, in queue indicator that displays calls in a queue specific manner to that agent's settings and preferences, 'Ready'/'Not Ready' status change indicators with 'not ready' reason code tracking, multi-line capability, ability to type and pass free-text message with transfers and conferences, conferencing with up to people, 'My Numbers' directory permitting for storage and organization of frequently called numbers, and call history for detailed information on all recent communications.

In operation, when an agent is logged into the application and is ready to receive a call, an agent status may change to 'Green' indicating their availability to other agents. When an agent is not ready, a 'Reason Code' may display various reasons for the unavailability including, 'Other Reason Codes' of 'Wrap Up', 'Break', 'Lunch', 'Work', 'Meeting', 'Training', etc.

When answering a call, the call can be answered using the 'Answer' button on the phone and a 'Tab' will display the phone number information of the caller. An active call will be enabled and will keep the call in a call queue even when the call is placed on Hold, a timer will illustrate how long the caller has been on hold. The toolbar may also illustrate separate hold times for the queue of callers.

In another example, call transfers and conferences may be used for live calls. A transfer may permit two parties to be on the line at the same time and may be used to transfer a call to a delegate or a queue, a message may be entered to provide a call indicator to the transferee party. Conference calls permit the delegate to be on the line with multiple parties. During a transfer a message can be entered to the receiving agent, a queue may be selected, an agent or number can be selected and for internal transfers, the message box can include a case #, caller & member name, reason for call, etc.

Calls within a queue may be illustrated with how many calls are in each queue, a skillset may be included to show the skill sets, wait times will update every 5-8 seconds in the pop up window, members may be preloaded into the application so that callers can be verified, All telephone calls may be logged so a record of the assigned agent is available, also the time spent on cases active, inactive, read only, etc., can also be logged. Additionally, priority processing may be used to sort, prioritize and manage queued messages and/or calls. Also, tabs and calls may be identified to track a total time of a case, to permit member demographic and contact management, to track case notes, manage which fields are required, maintain a history of case reassignments and other case activities, set case priorities, track outcomes of cases and interactions, track due dates, track follow-ups, sorting and filtering of a task list, track customer medical conditions, track the communication preference of the customer and agent, create follow-up tasks when emails are received, initiate selection of a case from a task list, assist in creating new cases from existing cases to reduce data entry, alert when a case is unlocked and can be edited, support capturing insurance information on the contact screen (required fields), support new member creation (real time), emphasize and track collaboration, customize case types for all services.

According to another example, when agents receive a phone call, request message or other communication message, through the application and the call enters the queue and is identified via a new tab, the application retrieves the caller information of the incoming phone number with known member database information to quickly locate the member's profile. If the customer/patient/member is not found in the database by the phone number or other identifier, a comprehensive search capability permits the agents to find the members in other ways. If the member is not in the database, the agent collects the demographic information from the member and adds them to the application system. Depending on the purpose of the call and the services offered to the client/member, the application supports any activity required to assist the member including coaching on gaps in care, assisting members on one or more cases from clinical and benefit issues, chronic care, wellness coaching, locating a physician, claims and appeals issues etc. Each "case type" guides the agent to the most efficient way of assisting the member and ensuring accurate and complete data collection. Correct demographic and contact information may be retrieved to inform a member of messages from their organization that their employer maintains as important, fax or email information may be used from a knowledgebase and document repository to members and for transfers to other providers in order to assist the member. For example, a case message or request may be escalated to a supervisor or medical director and past case notes can be retrieved and reviewed in real time. Agents can keep a number of cases active at a time and switch tabs to work with other members on other issues without losing work or being forced to have downtime waiting for assistance or feedback.

The system architecture may include three fundamental tiers including a data layer that is stored in a SQL Server. The tables, stored procedures/functions, and data can be referenced as needed. The next tier includes a WINDOWS communication foundation service hosted within a WINDOWS activation service under IIS 7.0. This configuration contains the business logic for changing data between tier 1 and tier 3. The WCF service includes a number of libraries (.dlls) containing code used to save the data to the database and present the data to the front end application. The tier 3 or presentation layer provides the actual application used by the agents. This portion is a '.NET' WINDOWS forms application that also uses WINDOWS presentation foundation. Each user has their own copy of the application which they run from the desktop.

Figure 2:
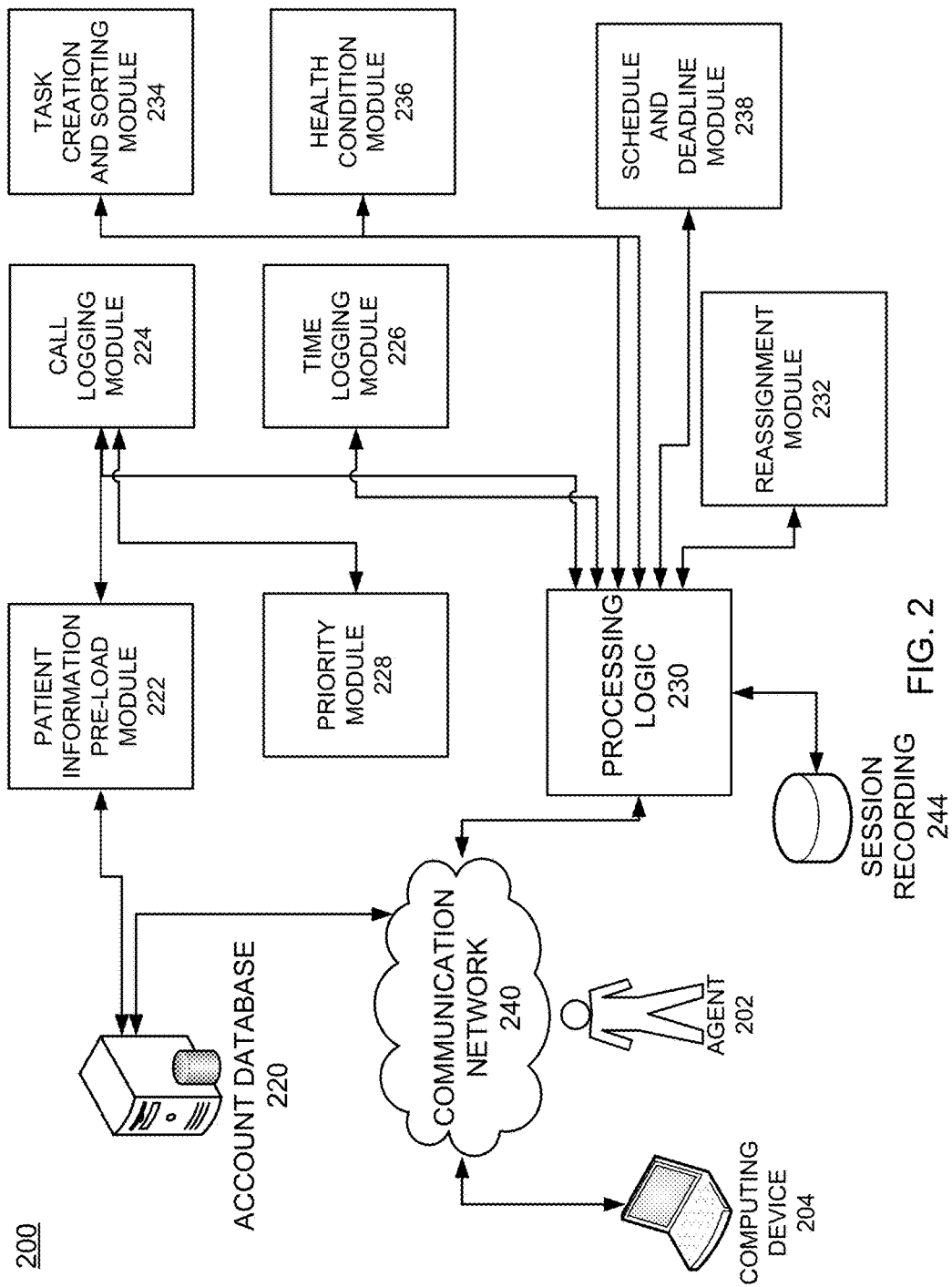
FIG. 2 illustrates an example agent communication and configuration network logic diagram according to example embodiments of the present application.

FIG. 2 illustrates an example agent communication and configuration network logic diagram according to example embodiments of the present application. Referring to FIG. 2, the network 200 includes an agent 202 accessing a computing device 204. The device may be a computer, laptop, mobile, wireless or cellular phone, a PDA, a tablet, a client a server or any device that contains a processor and/or memory, whether that processor or memory performs a function related to an embodiment of the application. The agent 202 may receive requests via the computing device 204 for a service/session and/or medical assistance. The requests may be from customers/patients/users who are seeking services. In this application, the types of services may be medical related for example purposes. However, one skilled in the art would appreciate that any type of service provider and service may be substituted and correlated with the example embodiments of the present application. The remote database server 220 stores agent preferences and customer records which can be readily accessed and used to setup a communication session across the communication network 240.

In operation, a user submitted request initiates an inquiry session or live call with the agent 202. The active call status may be initiated and the requesting customer may be entered into a queue which matches the customer with a customer record profile. The processing logic 230 may utilize a patient information pre-load module 222 that retrieves the patient record and pairs the caller with the record information. A customer may initiate a session via an email link, a short message service message (SMS), a phone call, etc. The priority module 228 may identify the customer and any information provided by the customer to setup an initial queue configuration that includes a relative priority level (e.g., 1-5 or 1-10) depending on the time the customer submitted a request, the urgency of the request, the chronic conditions assigned to the customer, the age of the customer, the initial request message information, etc.

Once a user profile is deemed 'active', the user profile may require an update to ensure the user's concerns are addressed properly. For example, the agent device 204 may receive a number of concerns relating to the user's current health and current concerns (e.g., types of pain, parts of the body experiencing pain, allergies, current prescriptions, last medical appointment, current location, current insurance, etc.). The processing logic 230 will then begin logging the call 224 and the time associated with the call 226. The customers' requests may be translated to tasks that are assigned to agents via the task creation module 234 and the customer's overall health 236 may also be identified and used to create one or more tasks or to prioritize the customer's current active request status or call status. Any subsequent appointments may be setup via the schedule and deadline module 238 and the reassignment module 232 may also be used to change agents in the event of a particular need or skillset requirement parsed from the customer request.

The processing logic 230 will identify the user's insurance profile 222 and the patient condition profiles 232 to ensure the results of the task creations are filtered by those user conditions. This provides a task delegation scheme that is in-line with the user's insurance network and payment plans. Also, a preliminary suggestion may be presented to the user based on a known user preference and/or a first objective identified by the agent.

In the event that the user conditions are more severe and require prioritization and status elevation in the active queue, then an automatic elevation in the queue position may be performed. For example, if the customer request is urgent and the health condition status is severe then the active callers in the queue may have the present customer record move up in the queue to a higher position sooner to be serviced by one or more agents. The queues which manage the user calls/messages with active statuses may have user records increased, elevated, and forwarded into a greater position, a higher position or a sooner to be answered position in the queue. All example of a greater queue position, a higher queue position or an elevated queue position may be interpreted by one skilled in the art to be a more favorable position and a sooner to be answered by an agent position. Severity may be elevated based on an identified condition, such as identifying the user input as "skin cancer" and parsing the term [cancer] from the message request. Severity may be a threshold that is compared to certain treatment options. A current queue position may be elevated for a first threshold level T1 ahead of other customers assuming the threshold T1 is an elevated position beyond regular queued requests. All customer requests records that are enacted as having an active status and are queued for agent review are recorded in a session recording database 244 for future reference.

Figure 3:
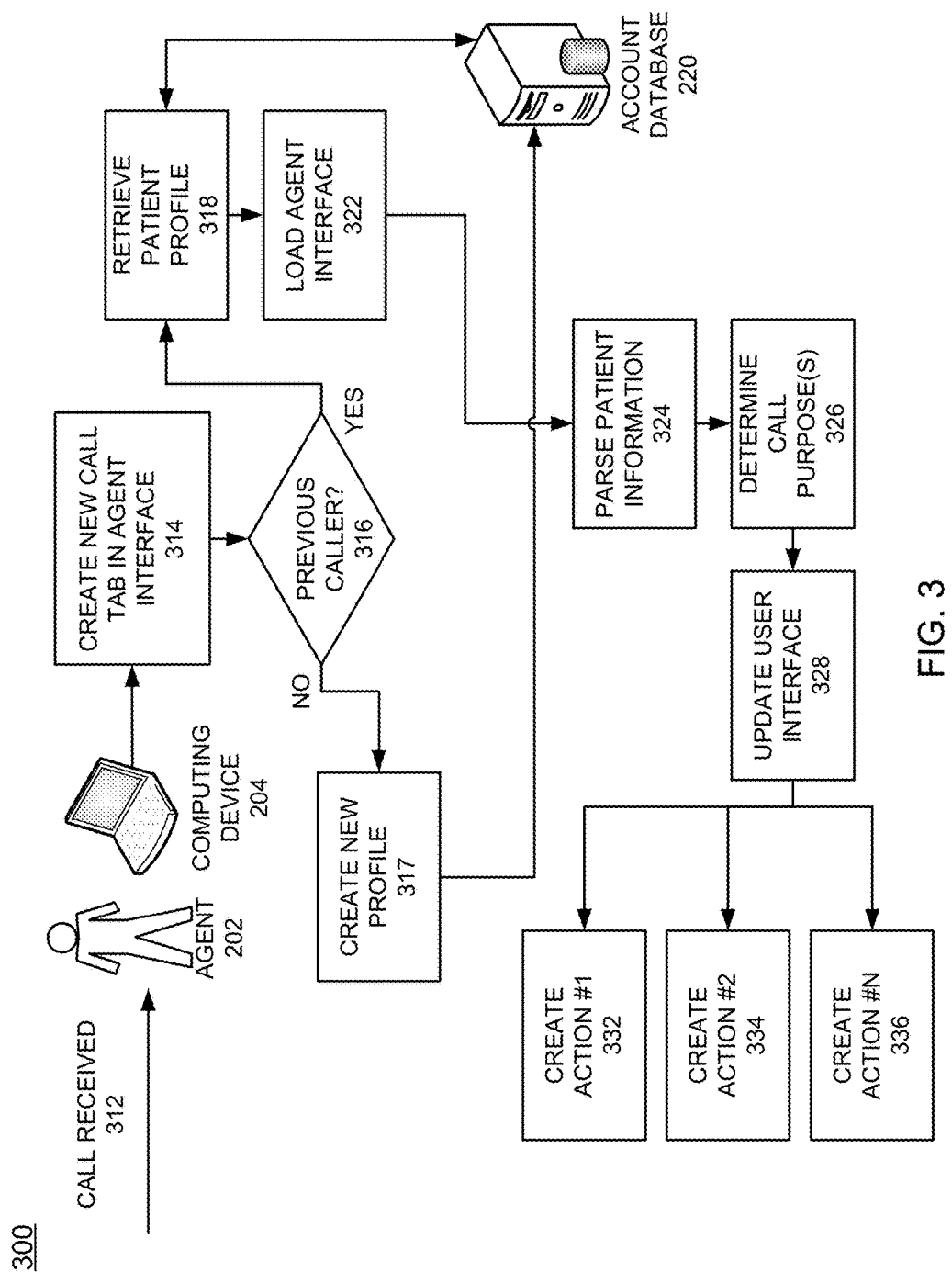
FIG. 3 illustrates a logic flow diagram and action diagram for processing a request via an agent platform according to example embodiments of the present application.
Figure 7:
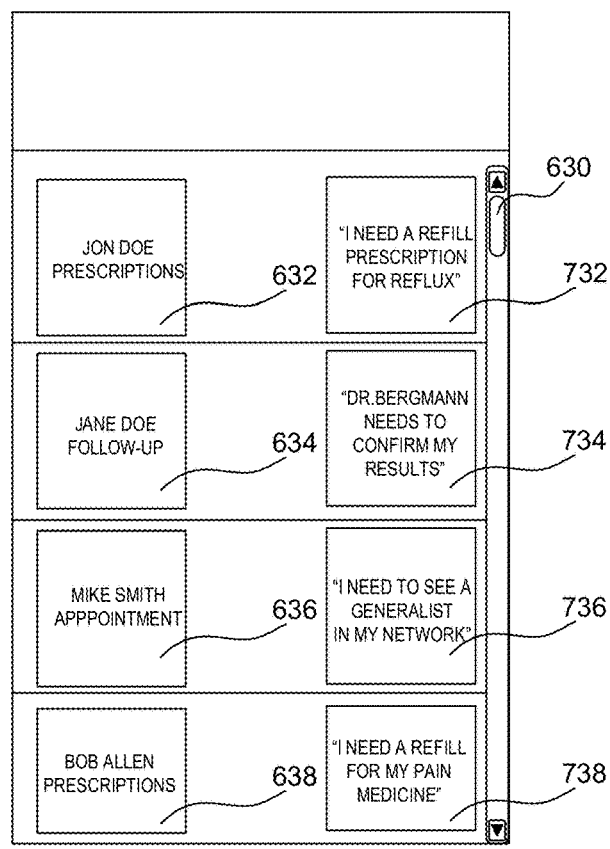
FIG. 7 illustrates a queue for customer request services according to example embodiments of the present application.

FIG. 3 illustrates a logic flow diagram and action assignment diagram for processing a request via an agent platform according to example embodiments of the present application. Referring to FIG. 3, the logic 300 begins with a call or message received from a customer 312 and assigned to an agent or an agent pool of agents 202. The customer number or other identifying information may be referenced from the request and paired with a customer record stored in the account database 220. The information is then used to create a new tab in the agent user interface 314. The customer is identified as either new or an existing customer 316. The patient profile 318 can be retrieved and used to load the agent interface with the new tab. Also, a patient message queue as illustrated in FIG. 7 may be a master queue that stores all active calls or active messages from various customers.

The agent interface can be loaded 322 with the customer information for ease of access and based on an initial priority condition. For example, an initial priority condition may be a first come first serve or first in first out (FIFO) queue configuration. When customers are not identified from previous calls, a new profile 317 may be created and used to create a new customer tab in the agent interface. The initial request call or message may include information about the purpose of the request, such as "I need a prescription refill", "I am supposed to follow-up with my doctor after the procedure", "I am having pain after the procedure/surgery", "I need to reschedule an appointment", "I need a new appointment". Any information provided by the customer may be provided as part of the SMS request message, as part of an email request message, as part of the call request message recorded by an IVR application and voice to text translation, etc.

The information provided with the request is parsed 324 and the purpose of the call is identified 326. The identification of the purpose may assist with pairing the correct agent with the correct skillset and with providing the information to a portion of the agent interface where the agent can quickly provide assistance. For instance, a particular purpose may populate a portion of the agent interface that is setup to receive specific information related to the request. In one example, the agent may have an interface customized where the need for "prescriptions" populates a designated portion of the user interface so the agent can review multiple tabs at one time seeking to assist customers that have information that pre-populates the agent's interface. Other agents may have other portions of their interfaces setup for other parsed information, such as appointments, etc., depending on the agent's preferences.

Once the purpose is ascertained from the message, the user interface will be updated with the new tab, updated with the needed information and the agent preference information for specific information audited by the agent. As a result, various actions 332, 334, 336 may be created to satisfy the customer requests. The actions may be setup for different customers or multiple actions may be setup for one customer depending on the message content. Once a number of requests are received and queued, the actions may be created for a particular agent based on the parsing of the message content.

Figure 4:
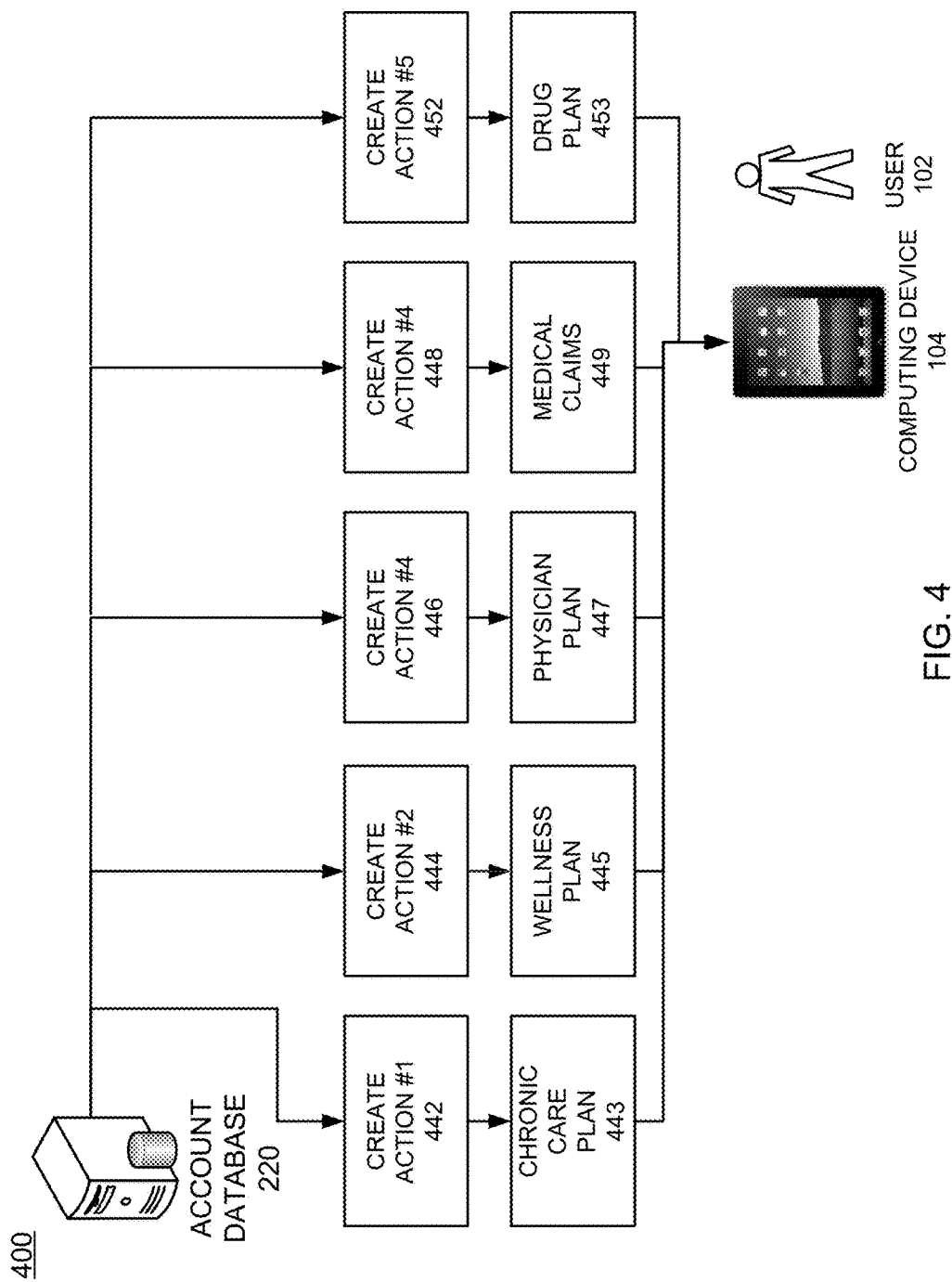
FIG. 4 illustrates another logic flow diagram and action diagram for processing actions via an agent platform according to example embodiments of the present application.

FIG. 4 illustrates another logic flow diagram and action diagram for processing actions via an agent platform according to example embodiments of the present application. Referring to FIG. 4, the actions can be created without any interaction with the customer. The actions can include modifications or additions to any customer record, including a first action 442 for changes or updates to a chronic care plan 443, a second action 444 for changes or updates to a health wellness plan 445, a third action 446 for changes or updates to a physician plan 447, a fourth action 448 for changes or updates to a medical claims issue 449, and a fifth action 452 for changes or updates to a drug plan 453. The interface of the agent may be updated to reflect the new actions automatically. The information from the request can prioritize the request, populate designated portions of a user interface of an agent and create tasks for the agent automatically without manual interaction of the agent and without a discussion between the agent and the customer. This enables the agent to assist the customers and even satisfy requests without ever answering a phone line, a satisfied request may return a text message or email to the customer device thus ending the active call prior to a live discussion.

Figure 5:
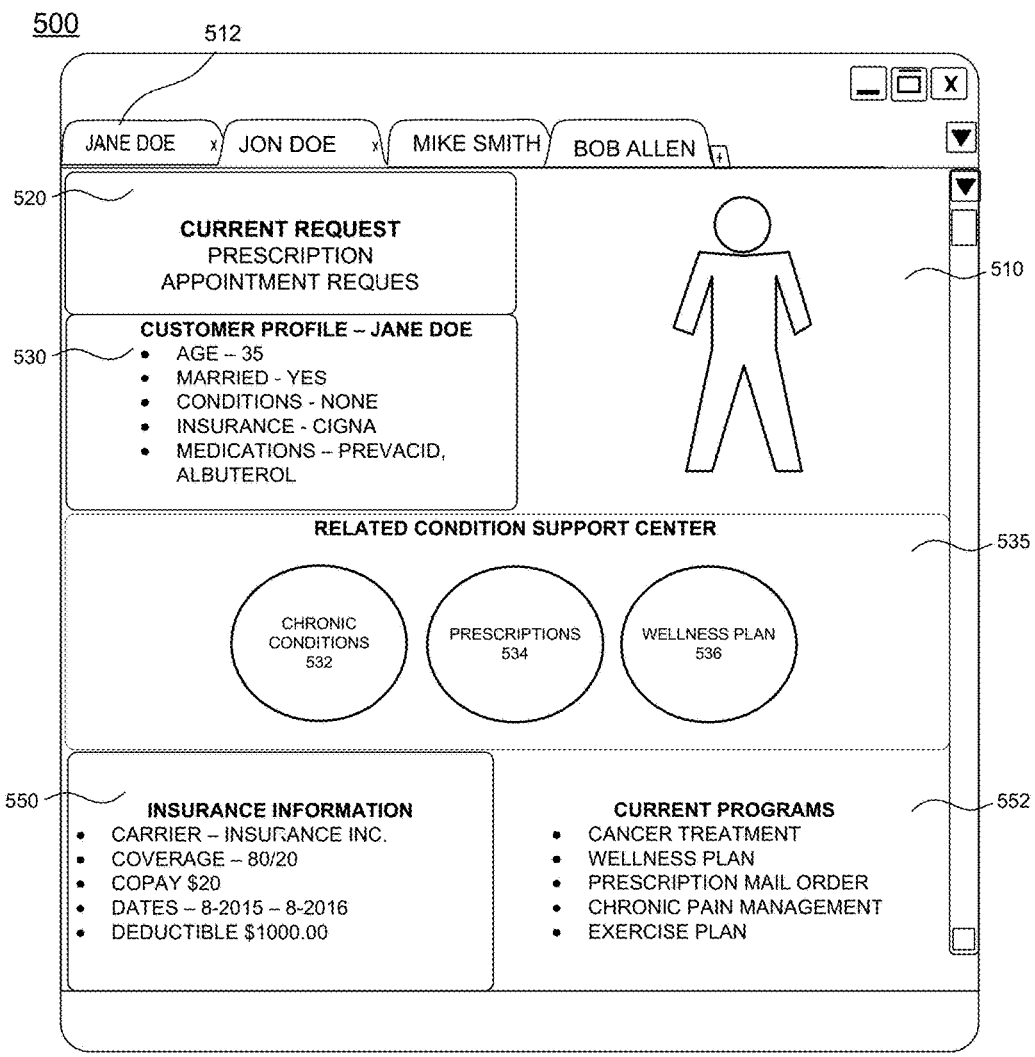
FIG. 5 illustrates an agent user interface populated with customer information according to example embodiments of the present application.

FIG. 5 illustrates an agent user interface populated with customer information according to example embodiments of the present application. Referring to FIG. 5, the user agent interface 500 has various dynamic and customizable attributes. For example, the tabs 512 at the top are active calls from customers with active message requests in the queue. The order of the tabs defaults to a FIFO approach, so the default would place the most recent request at the left of the tab row 512, however, elevated conditions, elevated requests and user agent preferences will reorder the tabs to accommodate ease of access and fulfillment by the agent and in an order consistent with elevated customer needs. In one example, an elevated or severely elevated customer need paired with a serious chronic condition, such as cancer, may create an elevate threshold level that place the message at the forefront of the tab order. However, in the absence of such elevated conditions, the agent profile may be referenced and utilized to order the tabs according to agent preferences, such as prescription refills first, since a request to reorder an existing prescription may be deemed the simplest task afforded to an agent depending on the agent preferences.

In this example, the agent preferences may place the current request information parsed from the request message at the top portion 520 of the agent user interface. The customer picture may populate another portion of the user interface 510. Also, a customer profile retrieved from customer history information 530 may populate another portion of the user agent interface by default or per an agent preference. Certain buttons or accessible links may populate another portion of the agent interface 535 with customer chronic conditions 532, prescriptions 534 and a wellness plan 536 depending on the customer profile and the agent preferences. Additionally, customer insurance information may populate another portion of the user interface 550 and current programs 552 may populate a last section of the user interface 552. Any or all of the portions of the agent interface may be based on agent preferences or customer urgency thresholds.

Figure 6:
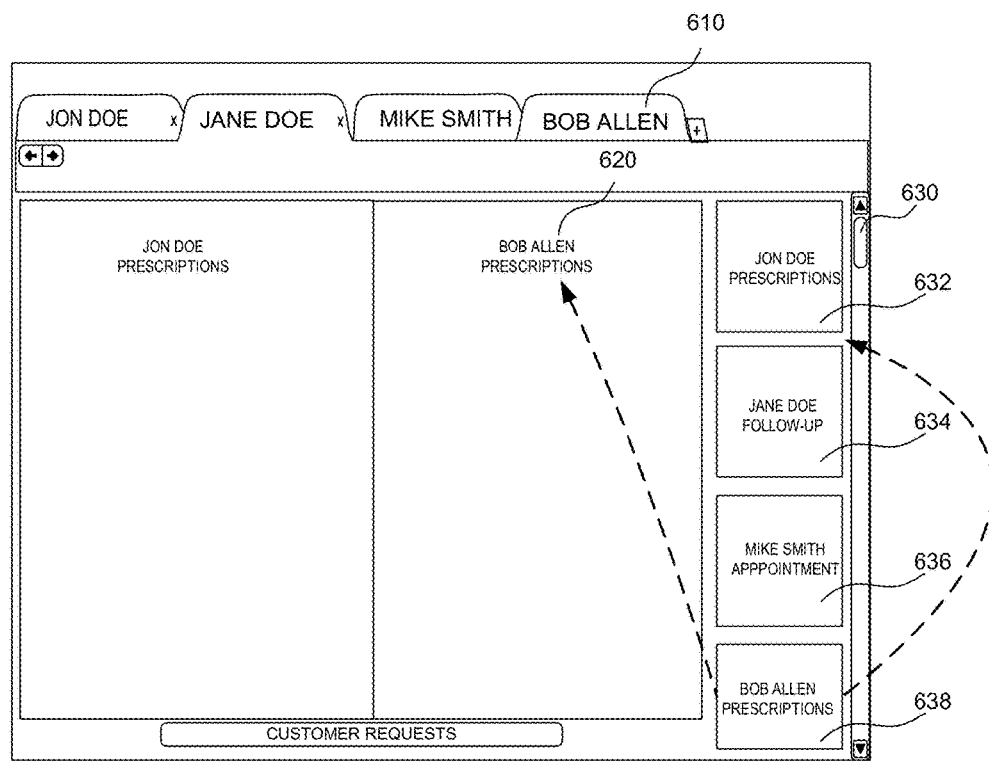
FIG. 6 illustrates an agent request interface with prioritized tabs displayed according to predetermined criteria according to example embodiments of the present application.

FIG. 6 illustrates an agent request interface with prioritized tabs displayed according to predetermined criteria according to example embodiments of the present application. Referring to FIG. 6, the agent interface 600 in this example includes tabs that have been populated based on an elevated priority associated with the customer request information. For example, the queue of active calls were populated in a queue scroll down side portion 630 of the agent interface. The four customers 632-638 are ordered based on a combination of the order the request was received, the severity of the request and the agent preferences. In this example, an agent preference to pair like requests in a side-by-side manner is illustrated. User 632 "John Doe" has first and had a prescription request type. The agent's preferences to pair like requests elevated user 638 to a second position behind user 632 since the requests were similar. The agent preference to pair like requests resulted in an elevated queue position of Bob Allen to be next behind John Doe. As a result, the agent may take a similar response action by fulfilling the request via transfer to pharmacy, physician task permissions, etc. Regardless, the agent can identify similar tasks and manage them in back-to-back to save time by consolidating a result for two customers at the same time or contemporaneous with one another.

FIG. 7 illustrates a queue for customer request services according to example embodiments of the present application. Referring to FIG. 7, the queue 700 includes the same four users 632-638 paired with request information 732-738 parsed from their request information. The queue by default may present the customers in a FIFO order, however, the patient severity index linked to the patient chronic conditions or other similar and serious patient history may elevate the patient to a higher level in the queue. This group of customers does not have an elevated index variable being assigned to any of the users since no one has a serious condition that can be identified by the chronic condition module of the processing logic. However, the agent preference may then be used to pair like requests for ease of addressing the concerns in an optimal manner.

Figure 8A:
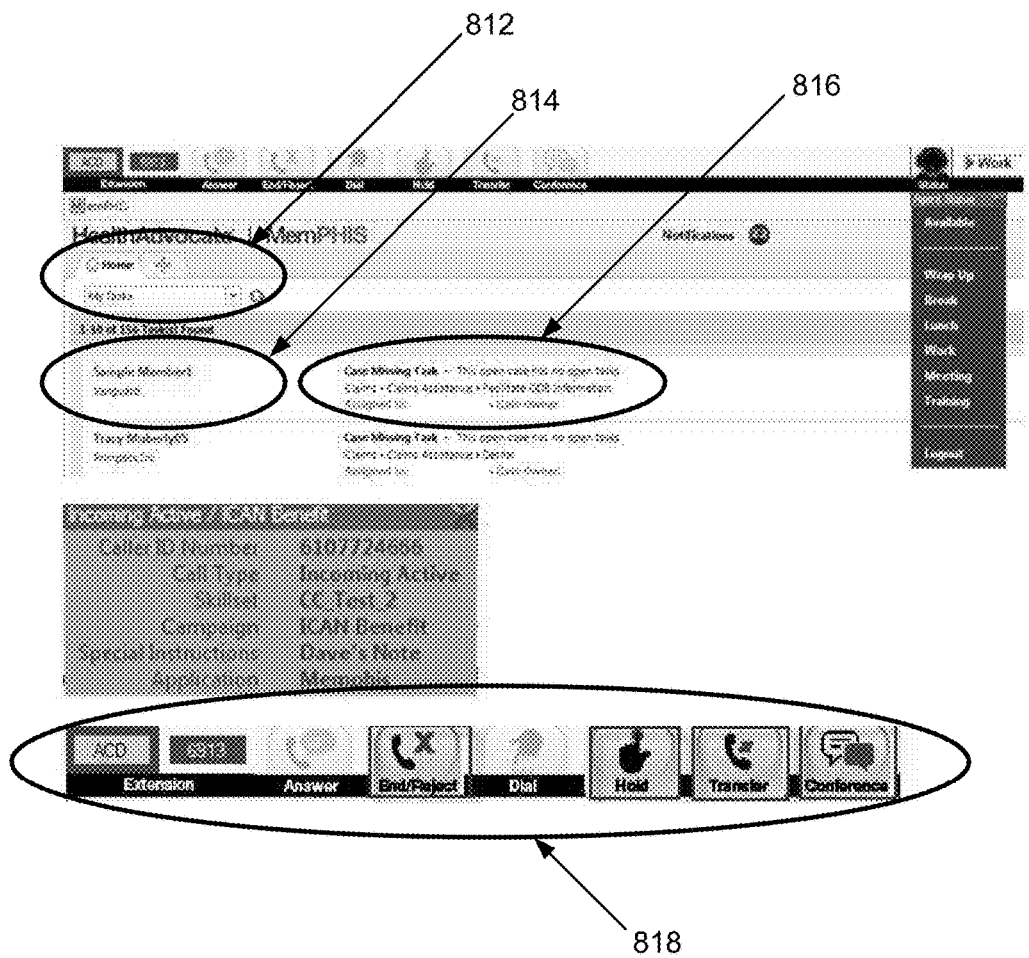
FIG. 8A illustrates a user agent interface according to example embodiments of the present application.

FIG. 8A illustrates a user agent interface according to example embodiments of the present application. Referring to FIG. 8A, the agent interface 800 includes a main home screen with a dropdown menu for tasks 812 that have been assigned to the agent based on incoming calls/requests. The example tasks are illustrated in the main display portion of the agent interface. For instance, a first task includes a member name 814 and a message portion 816 explaining the open task information. The bottom portion of the agent interface includes a call menu taskbar 818 with various call options to receive, transfer, hold and conference a particular call. Active calls can be readily managed by any of the access options in the taskbar 818.

Figure 8B:
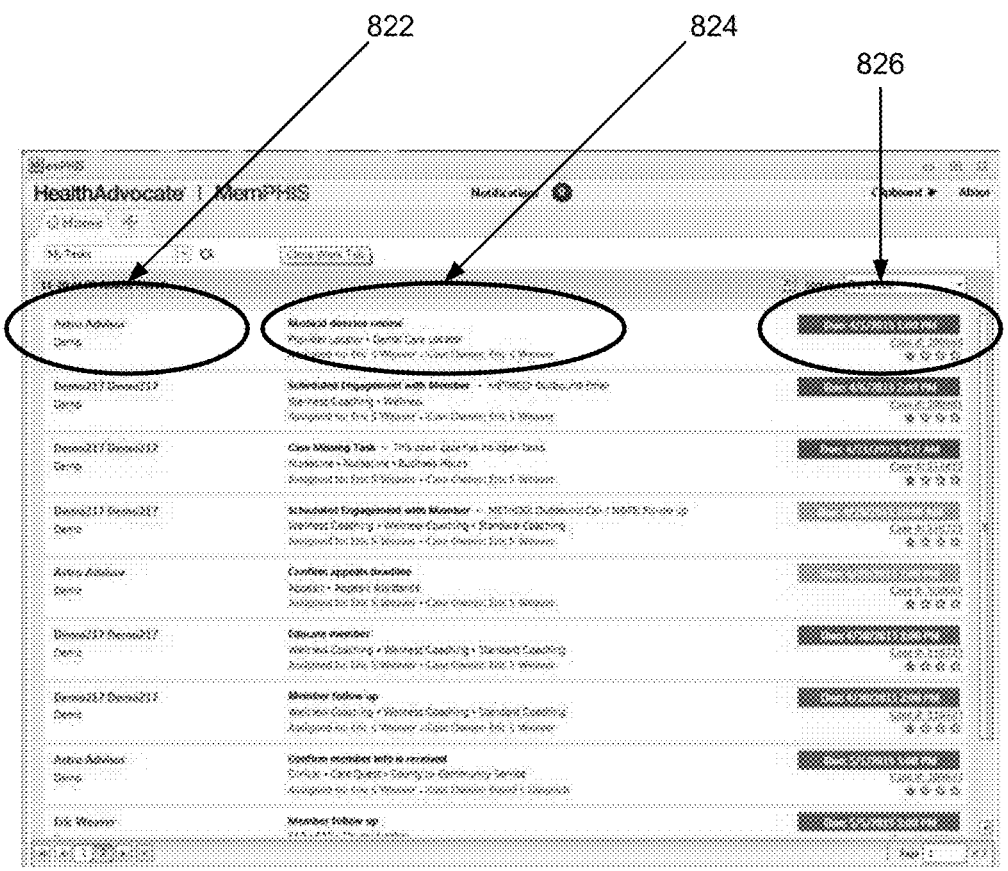
FIG. 8B illustrates another user agent interface according to example embodiments of the present application.

FIG. 8B illustrates another user agent interface according to example embodiments of the present application. Referring to FIG. 8B, the interface 820 includes a list of active tasks. The tasks all have a member name or customer name 822, a list of information 824, such as information that could be extracted and parsed from a user request message, and a call time, identifier and other metadata type information associated with a case file record 826 for the particular task and the corresponding user profile.

Figure 8C:
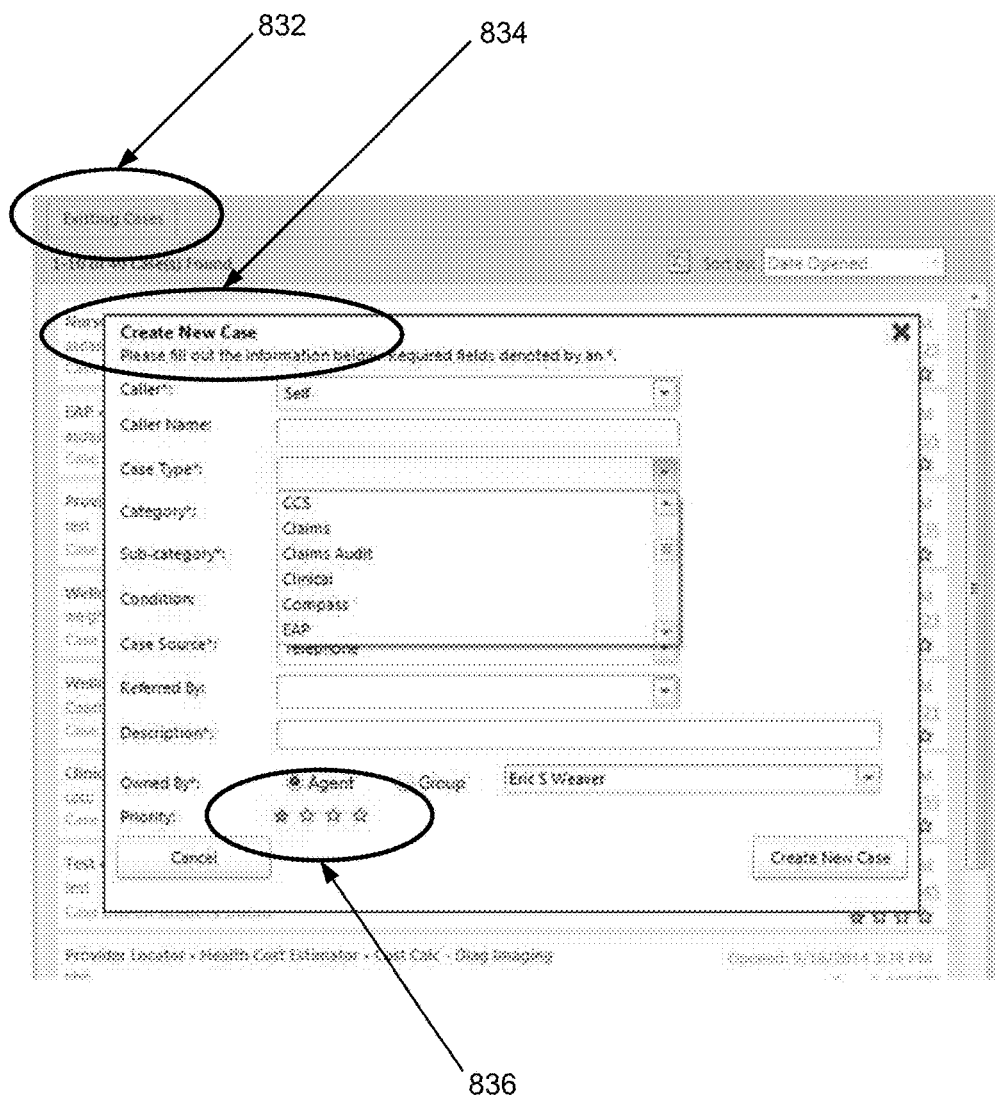
FIG. 8C illustrates yet another user agent interface according to example embodiments of the present application.

FIG. 8C illustrates yet another user agent interface according to example embodiments of the present application. Referring to FIG. 8C, the user interface 830 includes a case creation module and interface. The new case creation window 834 may be part of the existing cases menu 832. The priority 836 of the new case may be identified and set from the beginning of the case file. A case may be synonymous with a tab or active call procedure since the case that is created may be deemed active until further action by the agent.

Figure 8D:
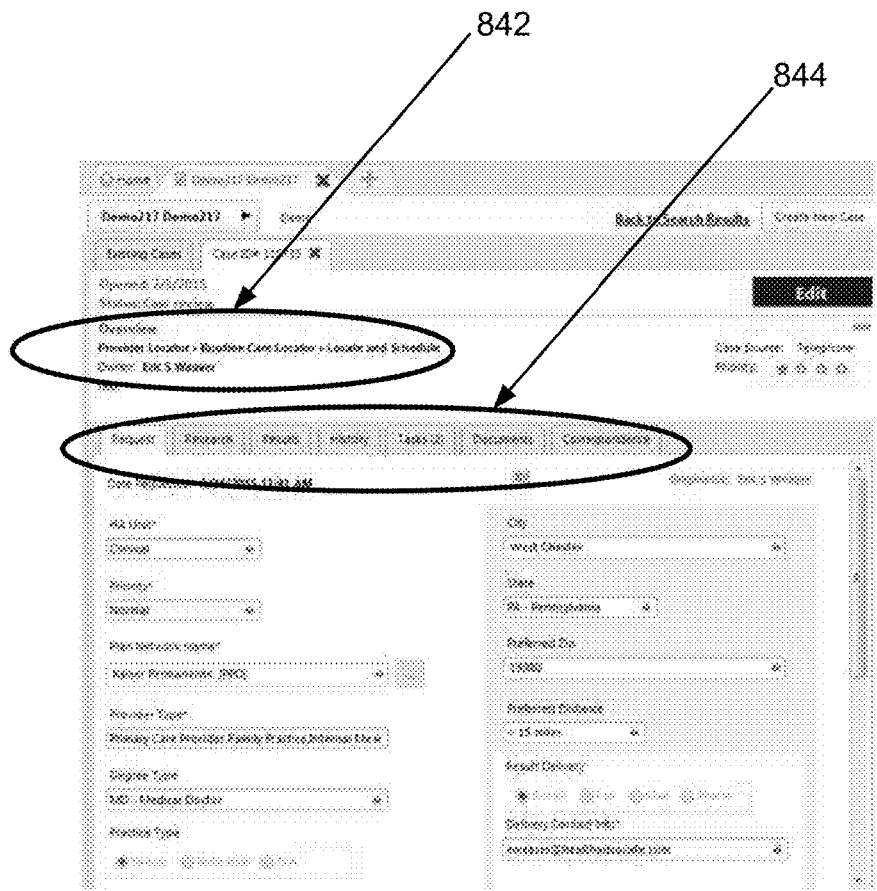
FIG. 8D illustrates still another a user agent interface according to example embodiments of the present application.

FIG. 8D illustrates still another a user agent interface according to example embodiments of the present application. Referring to FIG. 8D, the agent interface 840 includes a particular case identifier on the tab, an overview with information, such as the user or agent status of the case 842. Also, the user interface may have an additional section with cross referencing tabs to other information fields which are populated from the database information corresponding to the case identifier.

Figure 8E:
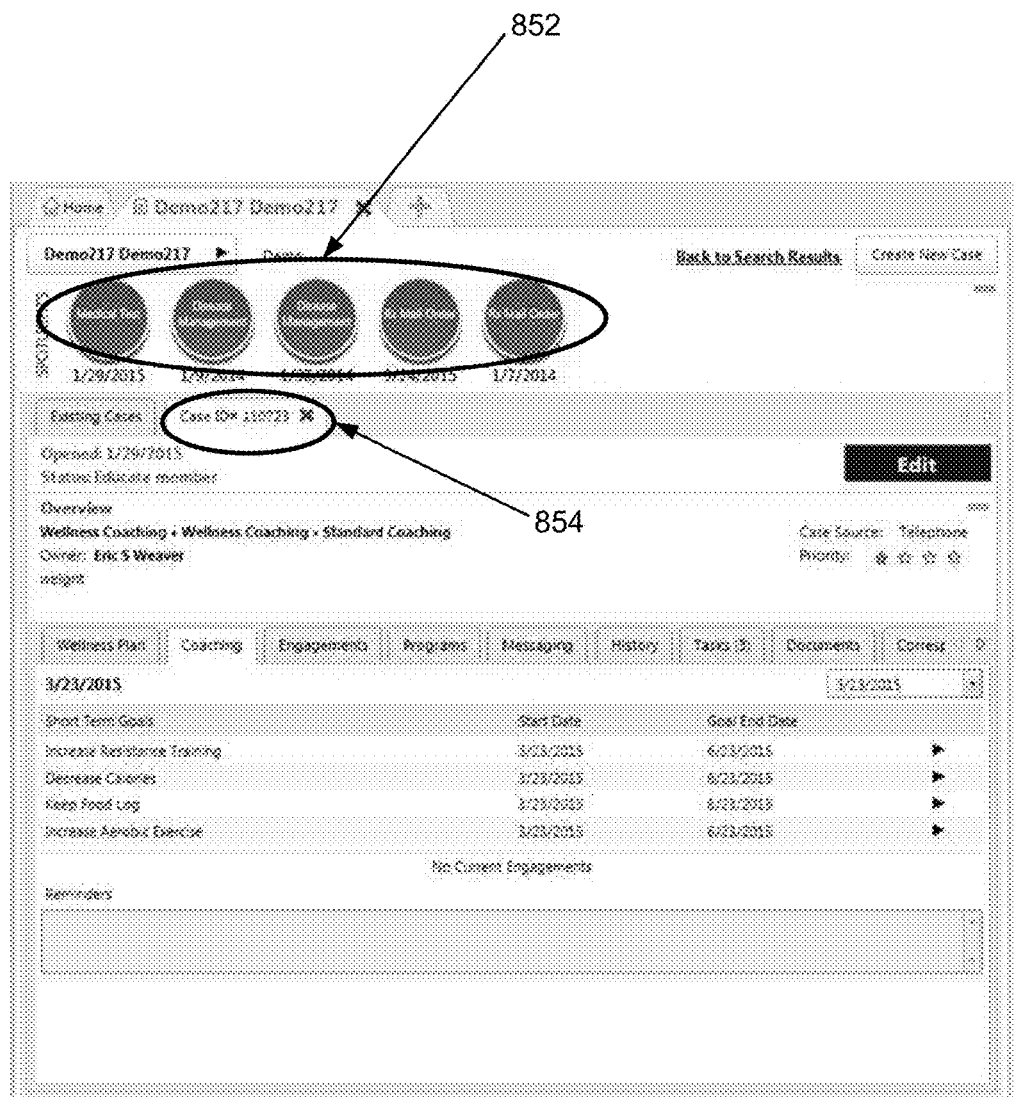
FIG. 8E illustrates still yet another user agent interface according to example embodiments of the present application.

FIG. 8E illustrates still yet another user agent interface according to example embodiments of the present application. Referring to FIG. 8E, the user interface 850 includes a list of buttons or links 852 which relate to previous events or sub-categories associated with a particular customer or case identifier 854. The quick access buttons 852 are linked to records and information related to previous sessions between the customer and the application agent services. An agent may quickly access any of the information in the user profile records via the control buttons on the agent display.

Figure 9A:
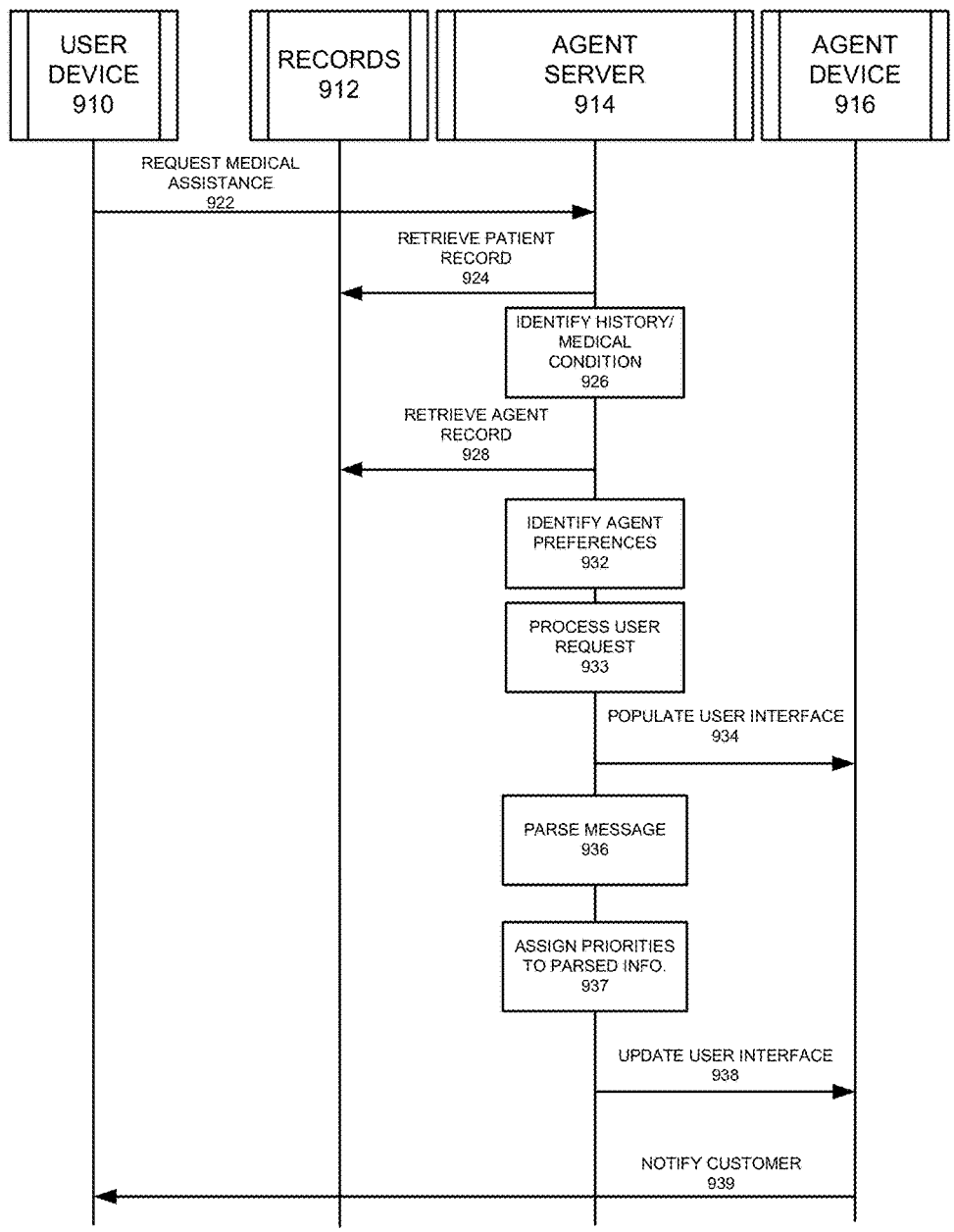
FIG. 9A illustrates a system signaling diagram for processing customer requests according to example embodiments of the present application.

FIG. 9A illustrates a system signaling diagram for processing customer requests according to example embodiments of the present application. Referring to FIG. 9A, the system configuration includes a user device 910 of the customer, a databank of customer records 912 which is party of the agent server network 914 and/or the agent server device 914 which hosts the application. Also, the agent device 916 is a separate computing device operated by the agent and in communication with the server 914 to communicate with the end user or customer device 910. In one example method of operation, the user device 910 may request medical assistance 922, the request may be received and responsive to receiving the request message a customer record may be retrieved 924 from memory to identify the medical condition information 926 associated with the customer. Also, an agent record 928 may be retrieved to apply agent preferences to the customer record creation and queue procedure. The agent preferences may indicate a preference for receiving the request messages/active calls and for loading the information into the agent queue and active tab portions of the agent interface. The agent preferences are identified 932 and the user request is then processed 933 prior to populating the user agent interface 934 on the agent device 916. The populated information may include customer information, customer request information, etc. The request information may be parsed and prioritized according to the agent preferences for certain terms in the message content. For instance, an agent may prefer appointment requests be placed in the queue first in order to assist with a continuous task cycle for optimal task completion. The message content of the message requests may be parsed 936 and priorities can then be assigned to the parsed information 937. All updates from parsing or with respect to receiving additional information may be updated in the agent device interface 938. The agent interface may then provide an optimal approach to an agent satisfying the request and forwarding the information to the user device 910.

During an agent interface populating operation, a first portion of the user interface may be populated with the request information parsed from the messages. This may be based on the agent preferences or a default configuration. Next, a second portion of the user interface may be populated with the customer information which is also based on predefined user agent preference information. For instance, the user agent may have a preference to have another portion of the interface populated with other customer information. Additional questions may be posed and transmitted to the user device and as supplemental information is received, the agent interface may be updated on the agent device.

When identifying agent preferences, at least one health condition associated with the customer record may be identified by the user agent preference information as a type of condition that is desired to be elevated in the queue, placed in a particular location of the dynamic agent interface, etc. As a result, a third portion of the user interface can be populated with the health condition specified by the agent and identified in the customer record. The health condition could include any one or more of a chronic condition, a prescription drug, and a previously identified health condition. The request message may include a short message service message, a phone call, and an email message or other communication medium message or active call/communication session. Additionally, the predefined user agent preference information may include a location on the user interface and a portion of the customer information specified to be displayed.

Once the customer information is known and the agent preferences have been identified, the request information may be parsed and priorities may be assigned to the health condition and the request information for queue placement. The health condition specified may then be inserted into a first portion of the user interface based on a priority assigned to the health condition, and the request information is then displayed in a second portion of the user interface based on a priority assigned to the request information. The priorities may also be assigned based on a condition severity ranking defined for conditions identified in the parsed request information and the at least one health condition.

Figure 9B:
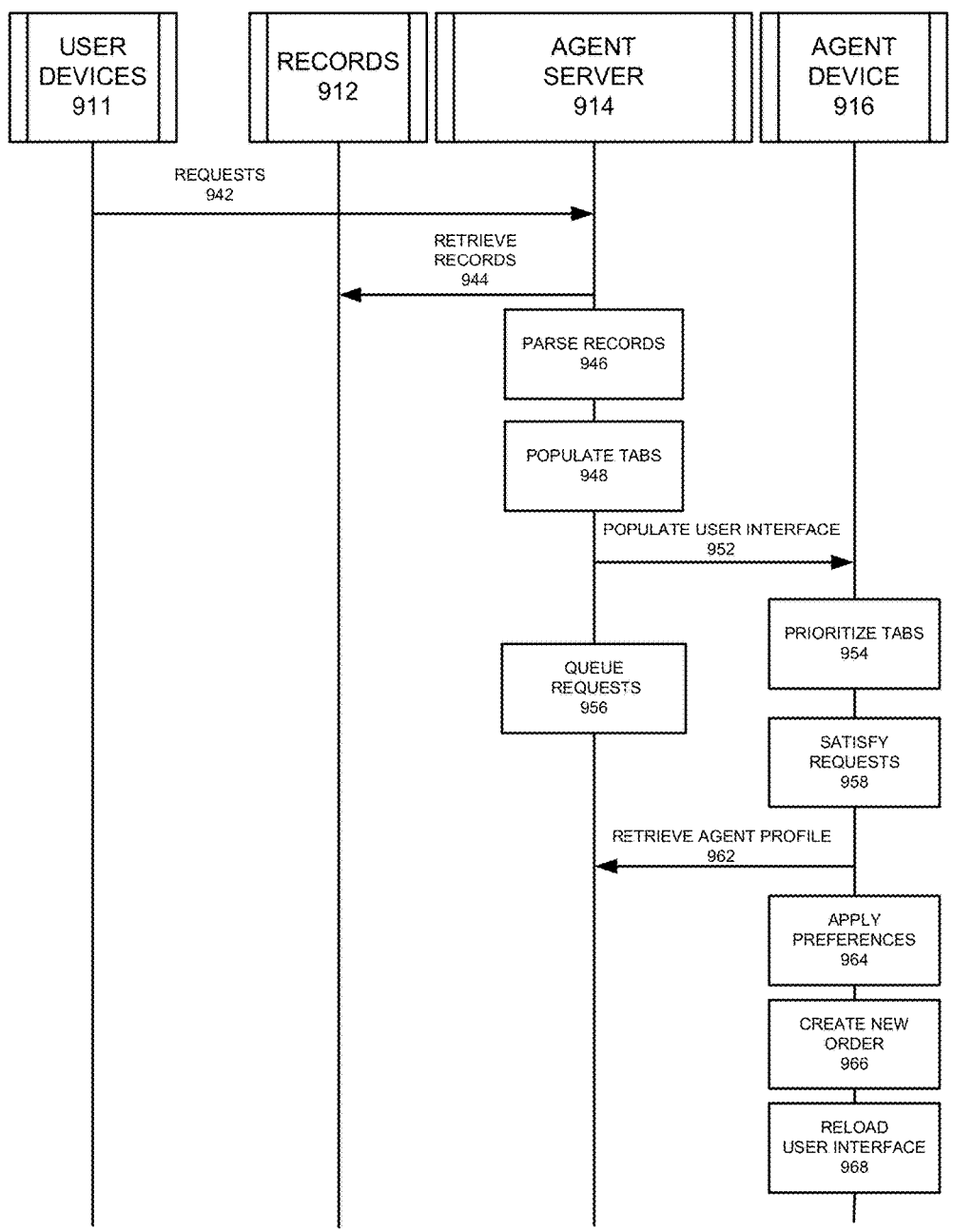
FIG. 9B illustrates a system signaling diagram for prioritizing customer requests according to example embodiments of the present application.

FIG. 9B illustrates a system signaling diagram for prioritizing customer requests according to example embodiments of the present application. Referring to FIG. 9B, the user devices 911 may be multiple customer devices sending requests for services to an agent server 914. The requests 942 may be received and customer records may be retrieved 944 from a records database 912. Next, a plurality of user interface tabs corresponding to the plurality of customer records may be created and setup on a user interface of an agent device. The tabs may be based on parsed information 946 of the request messages and tabs may be populated 948 based on the parsed information. The user interface 952 can then be populated and the tabs may be prioritized 954 according to the queue information. The queue requests 956 are identified and ordered and used to populate the tabs. The requests may be satisfied 958 and the agent profile can be retrieved 962 to apply the agent preferences 964 and to create a new order 966 given the preference information of the agent preferences.

Applying the preferences may cause the interface to reload with the new preferences and the reordered tabs based on the reordered queue of requests. For example, the plurality of request messages may be queued in a predefined order based on the content of the requests and the agent preferences, the user interface tabs may be arranged in a predefined order. One satisfied request among the plurality of requests may provide for modifying the predefined order to promote at least one user interface tab with a similar request to the satisfied request. In this example, as an agent satisfies a request, the preferences may indicate that content of the satisfied request may cause another queued message to elevate in the queue and populate the agent interface based on a similar content request, such as prescriptions, appointments, health conditions, etc.

In this example, an agent profile may be retrieved and at least one agent preference may be identified for ordering the user interface tabs. The at least one agent preference may be used by comparing the parsed terms to at least one term associated with the at least one agent preference. Then, by matching the term associated with the at least one agent preference to the parsed terms, a priority of the user interface tab that includes the matched term may be elevated. Then, a new order of the user interface tabs may be displayed on the agent computing device based on changes to the priority of the user interface tab.

Figure 9C:
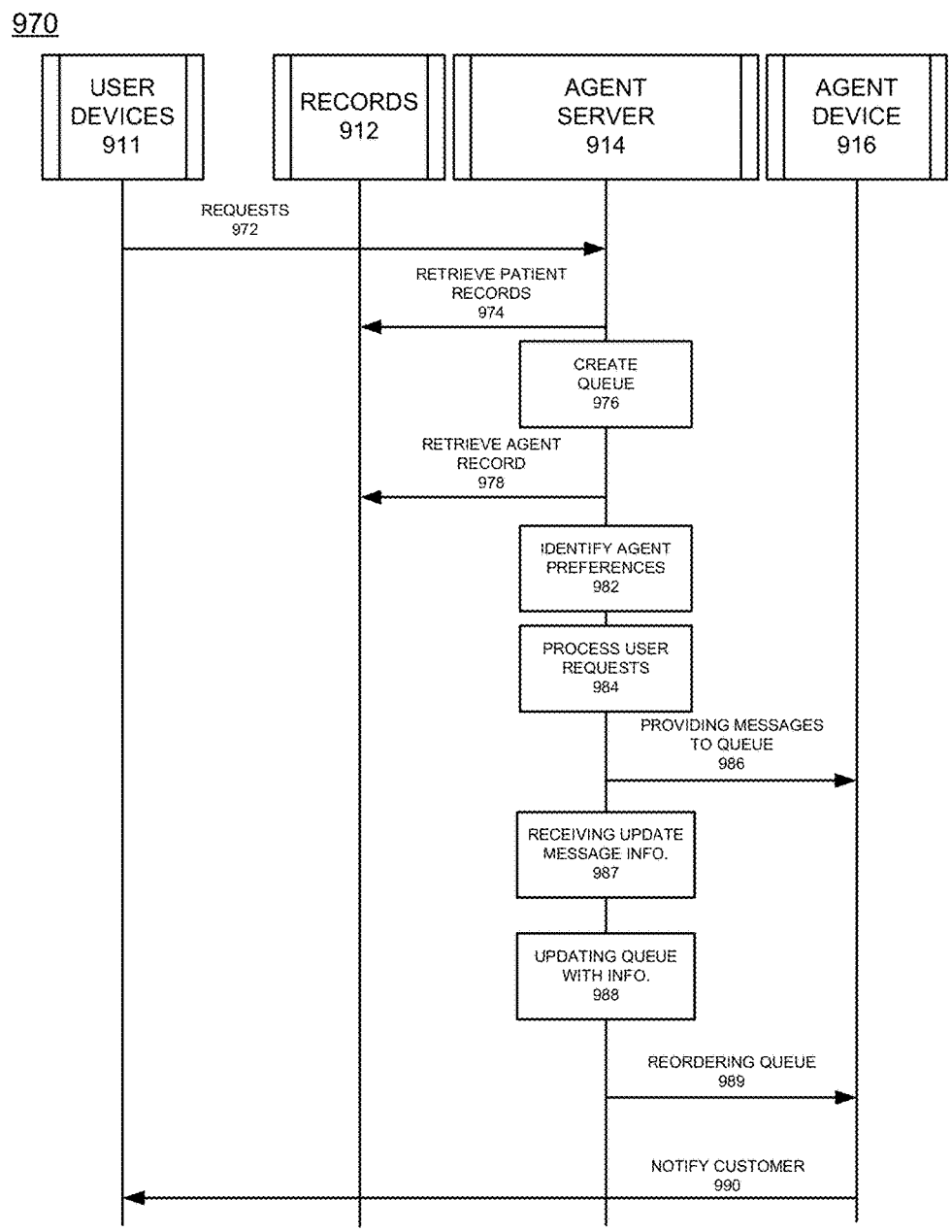
FIG. 9C illustrates a system signaling diagram for managing a queue of customer requests according to example embodiments of the present application.

FIG. 9C illustrates a system signaling diagram for managing a queue of customer requests according to example embodiments of the present application. Referring to FIG. 9C, the requests 972 received from the customers are used to retrieve records 974 and create a queue of messages/calls 976. Also, in this example agent records are retrieved to apply agent preferences 978. The agent preferences are identified 982 and used to process user requests 984 before providing the message queue to the agent device 986. The message content may be parsed from each of the plurality of request messages, and an order of the request messages can then be modified and prioritized in the queue based on the parsed content. Also, updated information 987 may be received causing an updated in the queue 988. The update may cause a reordering to occur and the interface to be updated accordingly 989. The customer may be notified of any satisfied requests thereafter 990. The customer attribute associated with each of the customer devices may include at least one of customer medical history information, customer name, customer contact information, customer chronic conditions and customer prescriptions. Also, prioritizing an order of the plurality of request messages in the queue based on the parsed content requests will require identifying a term from each of the plurality of requests and prioritizing an order of the plurality of requests based on the terms. An agent profile may be retrieved with one or more agent preferences for prioritizing the request messages. At least one request message including at least one term matching a term in the agent preference may be used as the basis for elevating the request above other requests in the queue. In certain circumstances, requests for additional information may be transmitted to the respective user devices responsive to receiving the request messages, next updated request information may be received from the plurality of user devices, and the queue may be updated with the updated request information. The process of updating the queue may include pairing the customer attribute with the updated request information as part of the message in queue. Thereafter, the queue order may be refreshed along with queue content responsive to receiving the updated request information, and the previous queue order may be reordered with the request messages to elevate the request in the queue including the updated request information to a higher queue position.

Figure 10:
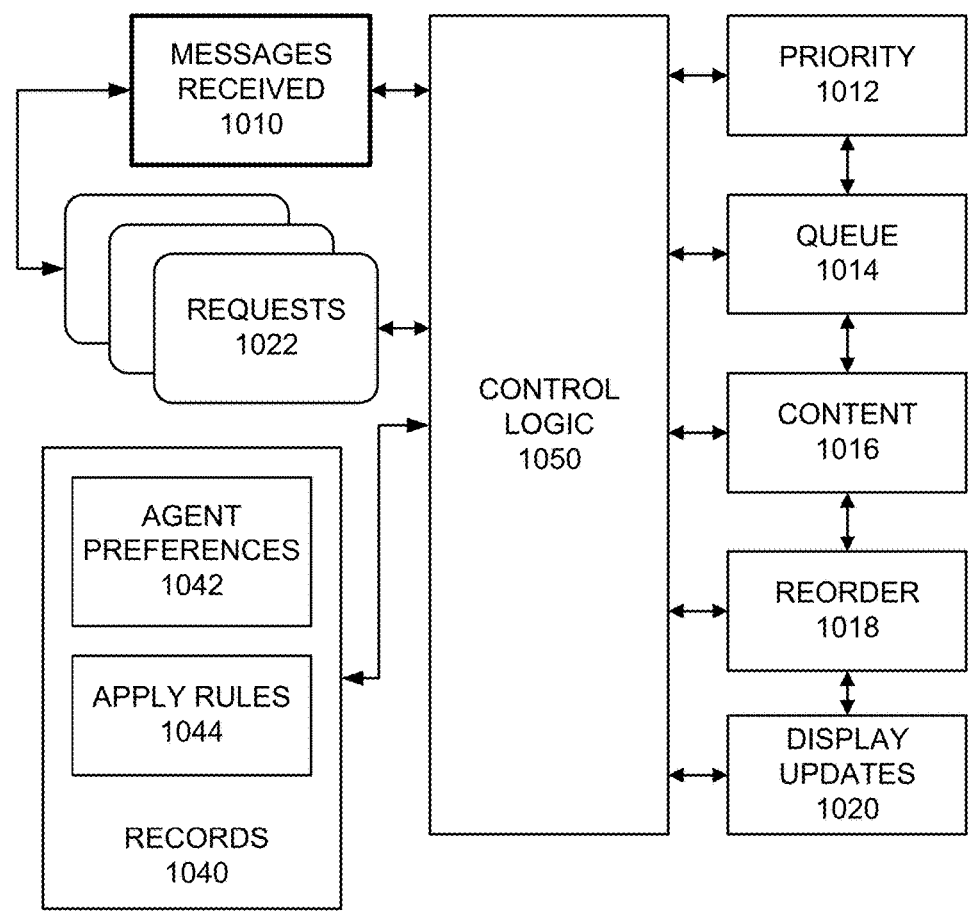
FIG. 10 illustrates a logic processing diagram according to example embodiments of the present application.

FIG. 10 illustrates a logic processing diagram according to example embodiments of the present application. Referring to FIG. 10, the logic configuration 1000 includes a control logic 1050 which may be a processor or other processing entity capable of receiving input and processing the input data to create output parameters. In this logic example, the customer requests 1022 triggers action by the processor 1050 based on content of the messages received 1010 and agent preferences 1042 which can invoke rules 1044 stored in records 1040 to be used to process message management output. For instance, the logic 1050 may create priorities 1012, queue configuration and ordering 1014, content analysis of the message 1016, updates and reordering of the queue messages 1018 and updates to the display 1020.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 11 illustrates an example network element 1100, which may represent any of the above-described network components of the other figures.

Figure 11:
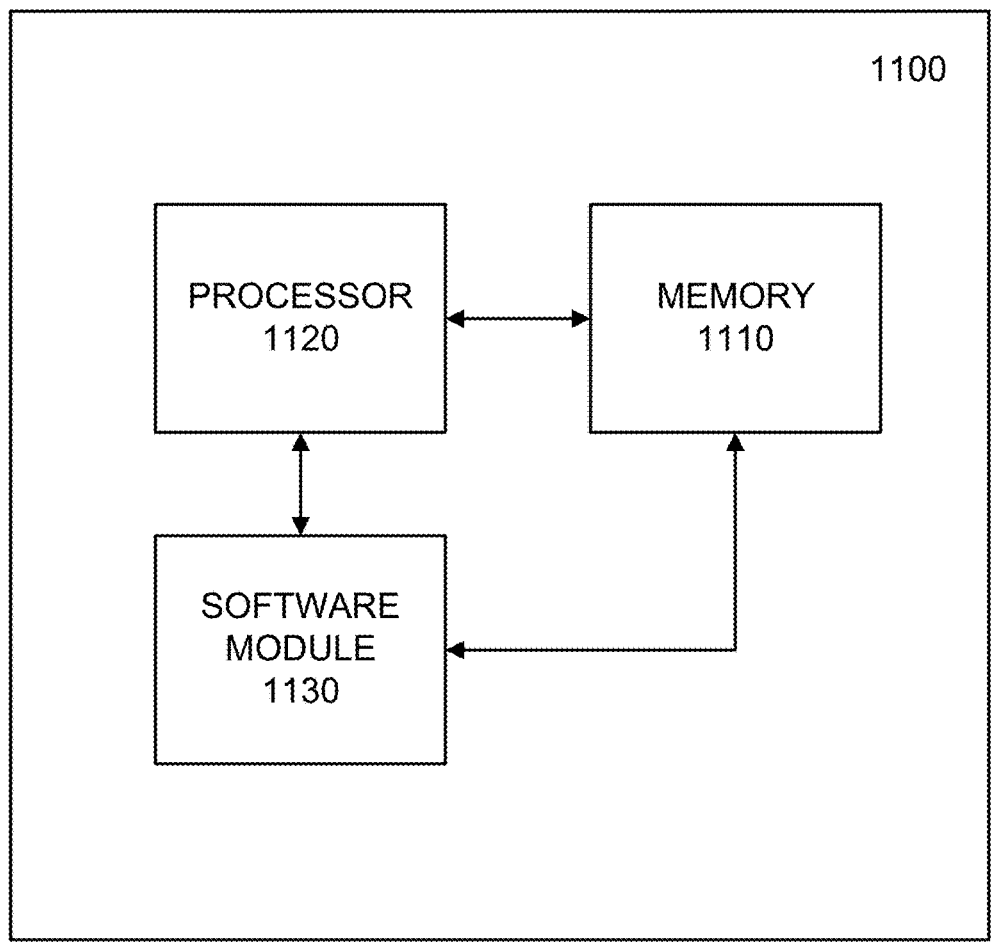
FIG. 11 illustrates an example network entity device configured to store instructions, software, and corresponding hardware for executing the same, according to example embodiments of the present application.

As illustrated in FIG. 11, a memory 1110 and a processor 1120 may be discrete components of the network entity 1100 that are used to execute an application or set of operations. The application may be coded in software in a computer language understood by the processor 1120, and stored in a computer readable medium, such as, the memory 1110. The computer readable medium may be a non-transitory computer readable medium that includes tangible hardware components in addition to software stored in memory. Furthermore, a software module 1130 may be another discrete entity that is part of the network entity 1100, and which contains software instructions that may be executed by the processor 1120. In addition to the above noted components of the network entity 1100, the network entity 1100 may also have a transmitter and receiver pair configured to receive and transmit communication signals (not shown).

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
   receiving a plurality of calls, including a plurality of messages, for customer service support from a corresponding plurality of customer devices at a call server, wherein the plurality of messages comprise customer information and customer request information;
   prioritizing an order of the plurality of calls based on a parsed content from the customer request information, wherein the prioritizing of the order comprises prioritizing according to an agent preference for certain terms in the plurality of messages;
   assigning the plurality of calls to a corresponding plurality of agent devices; and
   modifying the order of the plurality of calls based on changes to at least one of the customer status and agent availability.

2. The method of claim 1, wherein the at least one customer status comprises at least one of customer medical history information, customer name, customer contact information, customer chronic conditions, recently updated customer information and customer prescriptions.

3. The method of claim 1, wherein prioritizing an order of the plurality of calls comprises placing the calls in a queue based on the parsed content from call information associated with the calls and identifying at least one term from each of the calls and prioritizing an order of the calls based on the at least one term from each of the calls.

4. The method of claim 3, further comprising:
   retrieving an agent profile comprising at least one agent preference for prioritizing the calls; and
   placing at least one request message comprising at least one term matching the at least one agent preference above other calls in the queue.

5. The method of claim 4, further comprising:
   transmitting requests for additional information to the respective user devices responsive to receiving the calls;
   receiving updated request information from at least one of the plurality of user devices; and
   updating the queue with the updated request information.

6. The method of claim 5, wherein the customer status comprises at least one of an urgent health condition and a non-urgent health condition.

7. The method of claim 6, further comprising:
   refreshing the queue order and queue content responsive to receiving the customer status; and
   reordering the previous queue order of the calls to elevate the call in the queue comprising the updated customer status to a higher queue position.

8. An apparatus, comprising:
   receiving a plurality of calls, including a plurality of messages, for customer service support from a corresponding plurality of customer devices at a call server, wherein the plurality of messages comprise customer information and customer request information;
   prioritizing an order of the plurality of calls based on a parsed content from the customer request information, wherein the prioritizing of the order comprises prioritizing according to an agent preference for certain terms in the plurality of messages;
   assigning the plurality of calls to a corresponding plurality of agent devices; and
   modifying the order of the plurality of calls based on changes to at least one of the customer status and agent availability.

9. The apparatus of claim 8, wherein the at least one customer status comprises at least one of customer medical history information, customer name, customer contact information, customer chronic conditions, recently updated customer information and customer prescriptions.

10. The apparatus of claim 8, wherein prioritizing an order of the plurality of calls comprises placing the calls in a queue based on the parsed content from call information associated with the calls and identifying at least one term from each of the calls and prioritizing an order of the calls based on the at least one term from each of the calls.

11. The apparatus of claim 10, wherein the processor is further configured to
retrieve an agent profile comprising at least one agent preference for prioritizing the calls, and
place at least one request message comprising at least one term matching the at least one agent preference above other calls in the queue.

12. The apparatus of claim 11, wherein the processor is further configured to
transmit requests for additional information to the respective user devices responsive to receiving the calls,
receive updated request information from at least one of the plurality of user devices, and
update the queue with the updated request information.

13. The apparatus of claim 12, wherein the customer status comprises at least one of an urgent health condition and a non-urgent health condition.

14. The apparatus of claim 13, further comprising:
refreshing the queue order and queue content responsive to receiving the customer status; and
reordering the previous queue order of the calls to elevate the call in the queue comprising the updated customer status to a higher queue position.

15. A non-transitory computer readable storage medium configured to store instructions that when executed causes a processor to perform:
receiving a plurality of calls, including a plurality of messages, for customer service support from a corresponding plurality of customer devices at a call server, wherein the plurality of messages comprise customer information and customer request information;
prioritizing an order of the plurality of calls based on a parsed content from the customer request information, wherein the prioritizing of the order comprises prioritizing according to an agent preference for certain terms in the plurality of messages;
assigning the plurality of calls to a corresponding plurality of agent devices; and
modifying the order of the plurality of calls based on changes to at least one of the customer status and agent availability.

16. The non-transitory computer readable storage medium of claim 15, wherein the at least one customer status comprises at least one of customer medical history information, customer name, customer contact information, customer chronic conditions, recently updated customer information and customer prescriptions.

17. The non-transitory computer readable storage medium of claim 15, wherein prioritizing an order of the plurality of calls comprises placing the calls in a queue based on the parsed content from call information associated with the calls and identifying at least one term from each of the calls and prioritizing an order of the calls based on the at least one term from each of the calls.

18. The non-transitory computer readable storage medium of claim 17, wherein the processor is further configured to perform:
retrieving an agent profile comprising at least one agent preference for prioritizing the calls; and
placing at least one request message comprising at least one term matching the at least one agent preference above other calls in the queue.

19. The non-transitory computer readable storage medium of claim 18, wherein the processor is further configured to perform:
transmitting requests for additional information to the respective user devices responsive to receiving the calls;
receiving updated request information from at least one of the plurality of user devices; and
updating the queue with the updated request information.

20. The non-transitory computer readable storage medium of claim 19, wherein the processor is further configured to perform:
refreshing the queue order and queue content responsive to receiving the customer status; and
reordering the previous queue order of the calls to elevate the call in the queue comprising the updated customer status to a higher queue position, and wherein the customer status comprises at least one of an urgent health condition and a non-urgent health condition.

\* \* \* \* \*